US008655447B2

(12) United States Patent
Kukla et al.

(10) Patent No.: US 8,655,447 B2
(45) Date of Patent: Feb. 18, 2014

(54) SYSTEM FOR REMOTE PROGRAMMING OF A MEDICAL DEVICE

(75) Inventors: Volker Kukla, Berlin (DE); Joachim Reinke, Berlin (DE); Nicole Depping, Berlin (DE)

(73) Assignee: Biotronik CRM Patent AG (CH)

( * ) Notice: Subject to any disclaimer, the term of this patent is extended or adjusted under 35 U.S.C. 154(b) by 1326 days.

(21) Appl. No.: 12/167,400

(22) Filed: Jul. 3, 2008

(65) Prior Publication Data

US 2009/0012575 A1 Jan. 8, 2009

(30) Foreign Application Priority Data

Jul. 6, 2007 (DE) .......................... 10 2007 031 713

(51) Int. Cl.
*A61N 1/08* (2006.01)
(52) U.S. Cl.
USPC .................................. 607/30; 607/31; 607/60
(58) Field of Classification Search
USPC ................. 607/2, 3, 30–32, 60; 600/300–302
See application file for complete search history.

(56) References Cited

U.S. PATENT DOCUMENTS

| | | | |
|---|---|---|---|
| 4,676,248 A * | 6/1987 | Berntson | .......................... 607/59 |
| 4,740,890 A | 4/1988 | William | |
| 5,456,692 A | 10/1995 | Smith, Jr. et al. | |
| 5,588,146 A | 12/1996 | Leroux | |
| 5,822,771 A | 10/1998 | Akiyama et al. | |
| 6,442,432 B2 | 8/2002 | Lee | |
| 6,443,891 B1 * | 9/2002 | Grevious | ...................... 600/302 |
| 6,964,046 B1 | 11/2005 | Ogus et al. | |
| 2002/0032470 A1 | 3/2002 | Linberg | |
| 2002/0091417 A1 | 7/2002 | Splett et al. | |
| 2002/0196685 A1 * | 12/2002 | Topham | ........................ 365/200 |
| 2005/0283198 A1 | 12/2005 | Haubrich | |
| 2006/0031378 A1 * | 2/2006 | Vallapureddy et al. | ........ 709/208 |
| 2006/0074465 A1 * | 4/2006 | Webb | .............................. 607/60 |

FOREIGN PATENT DOCUMENTS

WO     WO 02/14 990 A1     2/2002

* cited by examiner

*Primary Examiner* — Eric D. Bertram
*Assistant Examiner* — Pamela M Bays
(74) *Attorney, Agent, or Firm* — Craig A. Fieschko, Esq.; DeWitt Ross & Stevens S.C.

(57) ABSTRACT

The invention consists of a system for remote programming of an implantable medical device such as a heart pacemaker, defibrillator or the like, wherein the system includes a programmable personal device (e.g., an implant) and a service center. The service center has a programming monitoring unit which determines a programming time endpoint which depends on the point in time at which a programming order was sent to the implant, and which cancels or deletes the programming order if the service center has not received a programming confirmation confirming successful receipt, execution, and/or forwarding of the programming order by the implant by the programming time endpoint.

20 Claims, 4 Drawing Sheets

SYSTEM FOR REMOTE PROGRAMMING OF A MEDICAL DEVICE

FIELD OF THE INVENTION

The invention relates to a system and a method for remote programming of a programmable personal medical device, in particular an implantable medical device such as a heart pacemaker, a defibrillator, a neurostimulator or the like. The system comprises at least a programmable personal device and a central service center as components. The personal medical device has a data communications interface which is designed so that the personal medical device can exchange data with the service center at least indirectly and bidirectionally. The service center also has a data communications interface to establish at least an indirect link to the personal medical device and thereby exchange data bidirectionally over this connection. Furthermore, this service center has a user interface, which is designed so that, with its help, programming orders for the programmable personal device can be compiled and sending of a compiled programming order can be triggered.

BACKGROUND OF THE INVENTION

Systems used in conjunction with heart pacemakers or defibrillators in some cases make it possible to transmit data obtained by a heart pacemaker or defibrillator, or their operational data, to a central service center to analyze these data there, and make these data available to an attending physician via a suitable user interface. Some functions of such implants are controlled by software or firmware and are therefore programmable. It often occurs that after initial reprogramming of the implant, additional programming or reprogramming is desired shortly before, during or after implantation, for example, to be able to adjust the implant better to possible health states of a patient that may have changed in the meantime, or to otherwise increase the efficiency of the implant. Such programming or reprogramming can be performed by a short-range wireless data link to an implant, established by a physician with the help of a programming device, wherein the physician programs the implant in the presence of the patient.

However, programming or reprogramming of the implant may also take place via the central service center. To this end, there is usually a data link between the service center and an intermediate patient device which is usually in the vicinity of a patient and can establish a bidirectional data link between the implant and the intermediate patient device. The link between the service center and the intermediate patient device may be established as a wireless or wired connection, e.g., via a telephone network.

A system for remote programming of implants is described in U.S. Pat. No. 6,442,432, for example.

SUMMARY OF THE INVENTION

An object of the present invention is to make essentially known systems and methods for remote programming of personal medical devices, in particular implants such as heart pacemakers, defibrillators or cardioverters, even more secure.

According to this invention, this object is achieved by a system of the type defined in the foregoing Background of the Invention section in which the service center has a programming monitoring unit that is designed to determine an ending point in time for programming, which depends on the point in time of sending of the programming order, and to delete a programming order that has already been sent if the service center has not received, by the ending point in time for programming, a confirmation of programming which confirms successful execution of the programming order on the part of the programmable personal medical device.

With such a programming monitoring unit, it is possible to ensure that once a programming order has been sent, it will not be executed in the case when it may already be obsolete. The invention takes into account the fact that 100% reliability cannot always be ensured for transmission of a programming order and that such a transmission may even take several days or weeks. In order for this problem not to result in a programming order that has already expired, leading to programming of the implant when this programming is no longer desired, the service center ensures that the programming order is deleted as soon as the ending point in time for programming has been exceeded and the programming has not been performed by then.

In the system, it is recognized that the programming may not be performed within the stipulated period of time because the transfer of the programming order, which may occur via multiple devices, is not completed. The transmission chain is often broken at some point. A programming order that has been sent is relayed further until the last device before the interruption and then remains stuck there to a certain extent. In such a scenario, it is very probable that a later program deletion order on the part of the service center will retrieve the previously sent programming order, namely at the device where the programming order was stuck due to the interruption in the transmission chain.

Accordingly, the service center is preferably designed to send a programming deletion order after the ending point in time for programming has elapsed if no confirmation of programming has arrived by the ending point in time for programming, such that the confirmation of successful execution of the programming of the implant, or at least the successful transmission to a respective personal medical device assigned directly to the implant, has arrived at the service center.

In addition to the service center and the programmable personal medical device, the system preferably also includes other devices, in particular an implant. The implant has an interface for wireless bidirectional data transmission between the personal medical device and the implant. A compatible data interface is provided with the personal medical device.

For such a combination, it is advantageous in particular if the programmable personal device is designed to forward a received programming order to the implant assigned to it and with each forwarding, to send a confirmation of forwarding as a confirmation of programming to the service center.

It is likewise advantageous if, on reception of a programming order by the service center, the personal medical device sends a confirmation of receipt as a confirmation of programming to the service center. In both cases, the personal medical device is preferably designed to add a time stamp in the form of data describing the point in time of forwarding of the programming order, or the point in time of reception of the programming order, to the respective confirmation of programming.

Accordingly, it is advantageous if the implant is also designed to send a confirmation of receipt to the service center via the personal medical device after receiving a programming order on the part of the personal medical device. The personal medical device is designed to forward this confirmation of receipt by the implant to the service center.

The implant in turn is designed to execute, if possible, a programming order after receiving it, i.e., to order a corresponding programming by itself. If this is successful, the implant preferably sends a success message to the service center via the programmable personal device. If the execution of the programming order, i.e., the installation of the corresponding program is not successful, the implant will send a message of failure to the service center via the personal medical device.

The service center is designed to receive confirmations of programming of a variety of types. To do so, the service center preferably has a database which contains entries about the respective status of the programming order together with the respective time stamp. Not only the last status but also several preceding statuses with the respective time stamps are preferably stored in the database.

The service center and/or its programmable monitoring unit may be designed to define and monitor a separate ending point in time for programming for each of the different transmission steps through which a programming order must pass.

As soon as one of these programming ending points in time has been exceeded without a respective confirmation of programming in this regard having arrived at the service center, the service center sends a corresponding programming deletion order, triggered by the programmable monitoring unit, causing the programming order sent previously to be deleted.

The service center and the respective programming monitoring unit are preferably designed to monitor multiple programming orders at the same time. In this context, it is advantageous if the user interface allows a user of one or more implants which are accessible via the service center and corresponding programmable personal devices to be selected.

With regard to the definition of an ending point in time for programming, there are several variants. A respective ending point in time for programming may be:
- individually definable by the physician for each reprogramming order,
- individually definable by the physician for each patient,
- individually definable by the physician for all his patients,
- individually definable by the physician for each implant model,
- individually definable by the physician for each product family,
- individually definable by the physician for each product type (tachycardia device, bradycardia device, CRT device or the like),
- individually definable by the physician for each disease syndrome that is assigned to the implant user,
- individually definable by the physician for each form of treatment assigned to the implant user,
- individually definable by the physician depending on the content of the reprogramming order, or it may be preselected at the service center, or through use of the remote programming, or it may be preselected according to the criteria given above in the service center or through the use of remote programming.

The invention may also include a service center for the system described above. The service center has a data communications interface for at least indirect connection of the service center to the programmable personal device and a user interface which is designed to compile programming orders for the programmable personal device and to trigger sending of a compiled programming order. Furthermore, the service center comprises a programming monitoring unit designed to determine an ending point in time for programming, which depends on the point in time of sending of the programming order, and to regard the programming order as failed if the service center has not received a confirmation of programming confirming successful execution of the programming order on the part of the programmable personal device.

The programming monitoring unit is preferably connected to a database, and is designed to perform entries for multiple ending points in time for programming for one or more personal devices, and/or one or more transmission or execution steps of a programming order, and to assign corresponding confirmations of programming with a time stamp to the database entries. It is especially advantageous when the user interface is designed as a remote programming application which is capable of running on a device remote from the service center as a function of a remote programming server unit and is designed to allow programming of multiple different personal devices, and has an input interface for selection of a device and for compiling a programming order for a selected personal device. The remote programming application may have an input unit for entering one or more ending points in time for programming for a respective programming order.

Another solution to the problem involves a method for remote programming of a programmable personal medical device, in particular an implantable medical device such as a heart pacemaker, defibrillator or the like by means of a system of the type described above. This method comprises the steps of:
- selecting a personal device to be programmed,
- compiling a programming order for the selected personal device,
- optionally determining at least one ending point in time for programming for the programming order, up to which point in time a transfer step of the programming order and/or an execution of the programming order should be concluded,
- optionally storing a fixed ending point in time for programming in the system up to which a transfer step of the programming order and/or an execution of the programming order should be concluded, which is used as a standard for all reprogramming,
- monitoring the respective ending point in time for programming by receiving and analyzing corresponding confirmations of programming, and
- automatic failure labeling of a programming order if a confirmation of programming belonging to a respective ending point in time for programming is not received by this ending point in time for programming.

An alternative solution to the problem involves the service center, in sending the programming order, adding data with one or more ending points in time for programming to the programming order. The devices involved in the transfer of the programming order in this version of the invention are designed on the basis of the ending point in time for programming attached to the programming order, and check on whether the programming order has arrived promptly at the respective device, i.e., before the ending point in time for programming which is valid for the respective device. If this is not the case, the respective device is designed not to forward or execute the programming order but instead to delete it. The last ending points in time for programming thereby define the ending point in time for programming which is valid for the respective implant, up to which point in time successful execution of the respective programming order must take place.

Additional advantageous versions of the invention involve use of a combination of features of the claims, as well as features discussed in the following description of a preferred exemplary version of the invention.

BRIEF DESCRIPTION OF THE DRAWINGS

The invention will not be explained in greater detail on the basis of a preferred exemplary version of the invention with reference to the figures, in which.

DETAILED DESCRIPTION OF PREFERRED VERSIONS OF THE INVENTION

Figure 1:
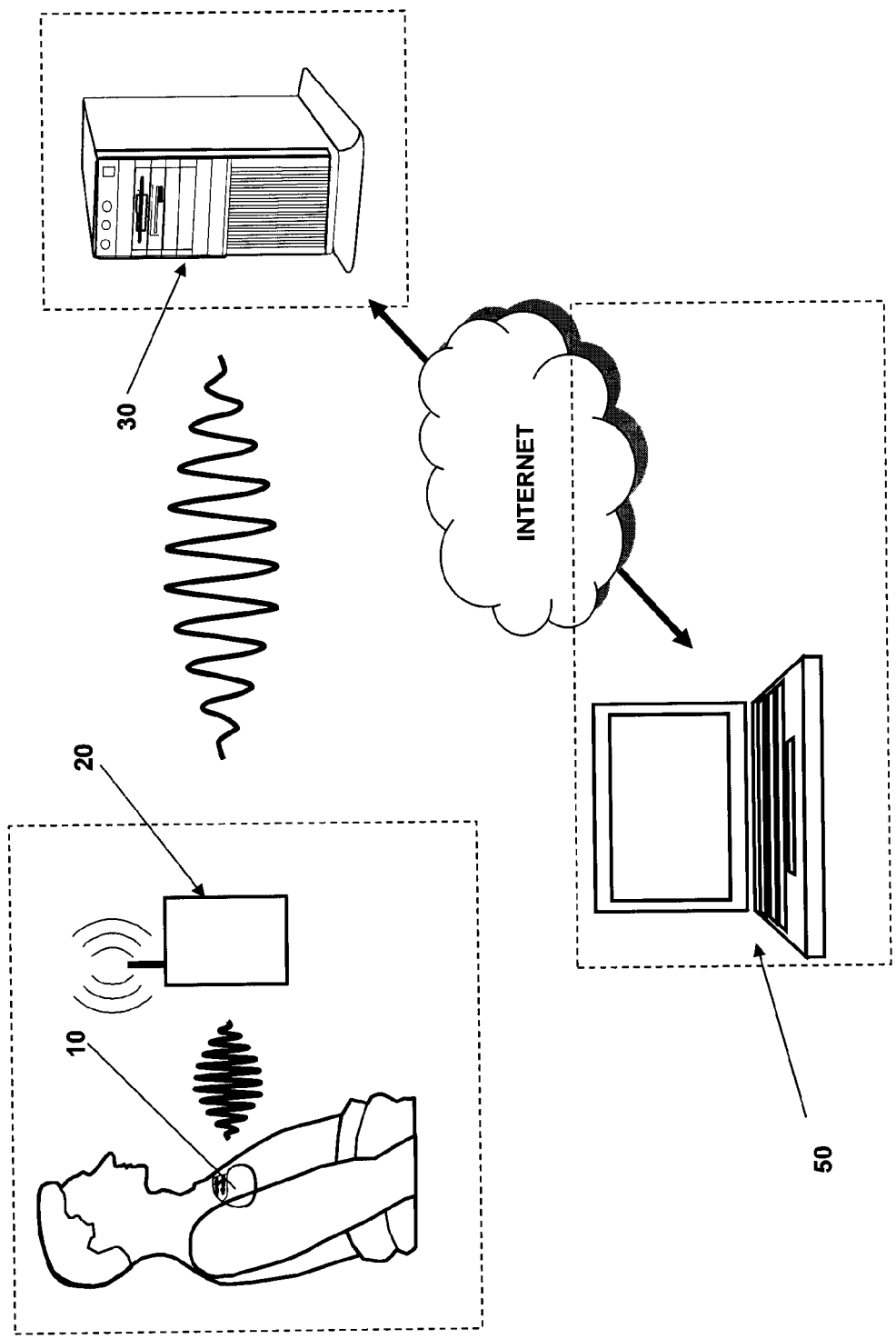
FIG. 1: shows an overview of a system for remote programming of implants.
Figure 2:
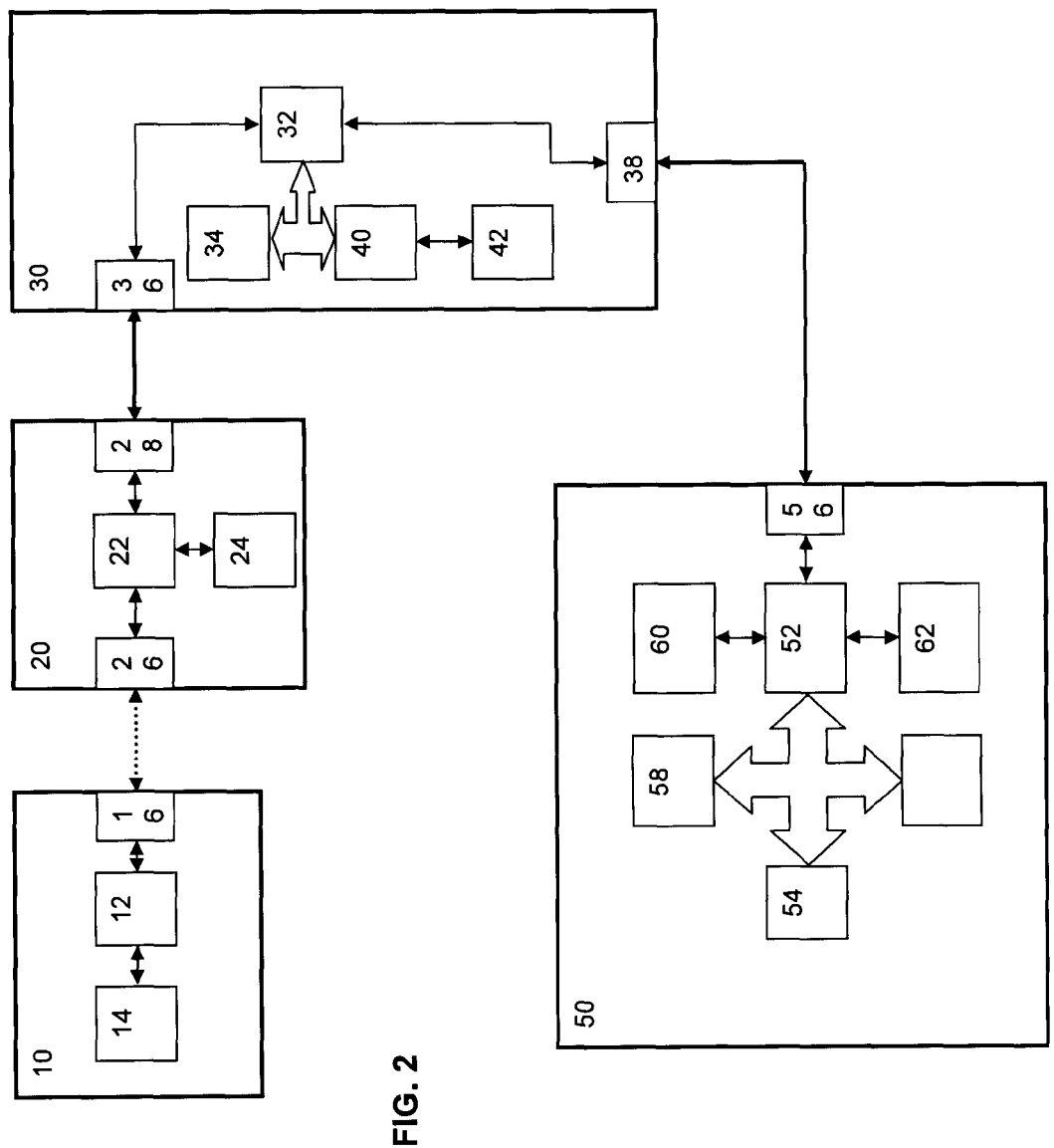
FIG. 2: shows block diagrams of preferred components, namely implant, intermediate patient device and service center.

FIG. 1 shows the components of an exemplary system for remote programming of implants. One component is the implant 10 itself. It has a controller 12 (see FIG. 2) which is connected to a memory 14 and also to a telemetry unit 16. The telemetry unit 16 allows wireless bidirectional data transfer to and from the implant 10.

Another component is an intermediate patient device 20 (FIGS. 1 and 2) which also has a controller 22 which is connected to a memory 24; to a first telemetry unit 26 for bidirectional data transfer to and from the implant 10; and a second data communications interface 28 over which the intermediate patient device 20 can exchange data bidirectionally with a central service center 30.

The central service center 30 (FIGS. 1 and 2) has, in addition to a controller 32, a central database 34 and a first data communications interface 36 over which the service center 30 can exchange data bidirectionally with the intermediate patient device 20. Furthermore, the central service center 30 has a remote programming server unit 40 which is connected to the control unit 32 of the service center, as well as to an Internet interface 38 for connection of a remote programming client 50. A programming monitoring unit 42, discussed below, is also included.

The remote programming client 50 has a central control unit 52 which is connected to a memory 54 and a data communications interface 56 for data transmission to and from the service center 30. Furthermore, the remote programming client 50 has a remote programming application 58 which can be executed with the help of the central control unit 52 and the memory 54, and can be run either as a stand-alone approach exclusively on the remote programming client 50 or, as a server application, partially or entirely accesses the central service center 30 and its remote programming server unit 40.

The remote programming application 58 makes it possible to compile programs 12 on the remote programming client 50 that can be executed by the implant 10 and its controller 12. The programs compiled in this way may be transferred in the form of a programming order from the central service center 30 to the implant 10 via the intermediate patient device 20.

To display the graphic displays generated by the remote programming application 58, the remote programming client 50 has a display screen 60. Furthermore, an input unit 62 is provided so that a user, e.g., a physician, can make entries for the remote programming of the implant 10.

Spatially the implant 10 and the intermediate patient device 20 are both situated in the vicinity of a patient. The central service center 30 is arranged at a central location. The remote programming client 50 is situated in the vicinity of a physician and can be a great distance away from the service center 30.

As already discussed above, in remote programming of the implant 10 with the help of the remote programming application 58 via the service center 30 and the intermediate patient device 20, there is the problem that the transfer of a programming order created with the remote programming application 58 may take a longer amount of time. For example, it may happen that the implant 10 is not situated in the vicinity of the intermediate patient device 20 for a certain period of time, or the service center 30 may for some reason be unable to establish a link to the intermediate patient device 20. It may also occur that a programming order tailored for a certain situation is no longer appropriate when it is no longer current after delayed transmission to the implant 10. To avoid this problem, the remote programming server unit 40 has a programming monitoring unit 42 which assigns an ending point in time for programming to each programming order.

The intermediate patient device 20 and the implant 10 are designed so that they each acknowledge the receipt of a programming order with a confirmation of programming, e.g., a confirmation of receipt. This confirmation of programming is sent back by the intermediate patient device 20 or the implant 10 to the service center 30. Each device, i.e., the intermediate patient device 20 or implant 10, adds to the respective confirmation of programming a time stamp in the form of data which indicates the point in time of receipt of the programming order. The remote programming server unit 40 stores the confirmations of programming received for a particular programming order together with the respective identifier of a respective device 10, 20 and the respective time stamp in the database 34.

When the implant 10 has finally executed a received programming order and has performed programming or reprogramming of itself, the implant 10 sends a confirmation of programming, e.g., a success message (or optionally a failure message), back to the service center 30. This confirmation of programming is likewise processed by the remote programming server unit 40, and the time stamp of the confirmation of programming containing the success message is compared with the ending point in time for programming for the respective programming order.

In parallel with that, the programming monitoring unit 42 of the remote programming server unit 40 regularly monitors the ending points in time for programming for individual programming orders. As soon as one of these ending points in time for programming has been reached and the respective success message of the corresponding implant 10 is not yet available, the remote programming monitoring unit triggers a deletion order which is designed so that it causes deletion of the programming order not yet executed. This ensures that a programming order is not executed at the wrong time.

Alternatively, the remote programming server unit 40 may also be designed so that it adds data to a respective programming order, where the data describe the ending point in time for programming. The intermediate patient device 20 as well as the implant 10 may be designed to check through their own control units 12, 22 on whether the ending point in time for programming of a respective received programming order has already been reached. If this is the case, the intermediate patient device 20 deletes the programming order via the implant 10 and does not forward it and/or does not execute it.

With regard to the definition of the ending point in time for programming, there are different variants. A respective ending point in time for programming can be defined by the physician himself via the remote programming application 58. In this case the remote programming application 58 is designed so that it allows a corresponding input. The remote programming application 58 may also be designed so that with its help fixed ending points in time for programming for a respective implant 10 are to be defined. This is expedient in particular when a physician is treating not just one implant 10 but several. The remote programming application 58 may also be designed, so that a physician defines an ending point in time for programming—calculated from the point in time of sending the programming order—for all implants 10 managed by that physician in his practice.

Another alternative involves the remote programming application 58 allowing various ending points in time for programming to be predefined for different implant models or model families.

Another alternative involves the remote programming application 58 making it possible to define different ending points in time for programming for different product types, e.g., heart pacemakers or defibrillators or for different types of programs.

In addition, the remote programming server unit 40 may be designed to automatically determine a suitable ending point in time for programming for a respective programming order. To do so, corresponding data, e.g., assigned to individual patients or devices, may be stored in the database 34.

It is possible in particular that the remote programming server unit 40 assigns multiple ending points in time of programming to a programming order such that they are assigned to different devices and/or transmission steps and processing steps of a respective programming order. For example, it may be possible with the example described above to define an ending point in time for programming for reception of the confirmation of programming with the confirmation of receipt of the intermediate patient device 20, another later ending point in time for programming for receipt of the confirmation of programming and the confirmation of receipt of the implant 10, and finally a third even later ending point in time for programming for receipt of the confirmation of programming with the message of success of the implant 10.

A few variants for a determination of the ending point in time for programming are listed below. The ending point in time for programming may be:
  definable individually by the physician for each reprogramming order,
  definable individually by the physician for each patient,
  definable individually by the physician for all of his patients,
  definable individually by the physician for each implant model,
  definable individually by the physician for each type of product (tachycardia device, bradycardia device or CRT device, etc.),
  definable individually by the physician for each disease syndrome which is assigned to the implant user,
  definable individually by the physician for each type of treatment assigned to the implant user,
  definable individually by the physician depending on the content of the reprogramming order, The ending point may also be defined fixedly in the service center or through the remote programming application, or defined according to the aforementioned categories in the service center or by the remote programming application.

Alternatively, there may be separate ending points in time of programming for each of the partial links of data transmission described below. For example, the ending point in time for programming may allow 24 hours for transmission from the service center to the intermediate patient device, and the other ending point in time may allow 72 hours for the transmission from the intermediate patient device to the implant.

Programming of an implant 10 may be performed by the foregoing system by, for example, the following steps:
1. With the help of the (web) application service center 30, the physician selects an implant 10 and compiles a new/modified program for it.
2. The physician sends this program as an order for programming from a remote location.
3. The service center 30 adds the preset ending point in time for programming to the received order.
4. The service center 30 sends this order over an existing data link (e.g., GPRS, UMTS, GSM, modem, etc.) to the intermediate patient device 20 and stores the time stamp of this transmission as well as the prevailing status (e.g., "order transmitted to intermediate patient device").
5. The intermediate patient device 20 sends a confirmation of programming concerning receipt of the order back to the service center 30 which in turn stores the time stamp of receipt of the confirmation of programming, as well as the prevailing status (e.g., "receipt of the order from the intermediate patient device confirmed").
6. The intermediate patient device 20 now attempts to transmit the order to the implant 10 via a radio data link and, informs the service center 30 about each of these attempts with a corresponding confirmation of programming. The transmission to the implant 10 may be repeated according to a certain scheme.
7. The service center 30 stores the time stamp of the attempts by the intermediate patient device 20 to transmit the order to the implant 10, and stores the current status (e.g., "transmission of the order to the implant successful/not successful") in the database 34.
8. The implant 10, upon receiving the programming order, and confirms receipt to the intermediate patient device 20.
9. The implant 10 attempts to activate the program received and sends a confirmation of programming regarding the success or failure of this action to the service center 30 via the intermediate patient device 20.
10. The service center 30 stores the time stamp and the status of activation of the program transmitted with the programming order (e.g., "activation of the programming order successful/not successful") in the database 34.
11. The physician may obtain information about the prevailing status of the programming order with the help of the remote programming application 50 via a query of the database 34.

Steps 4-9 are performed only if the ending point in time for programming contained in the programming order has not yet expired. As soon as the ending point in time for programming has expired, the component that is currently in possession of the order discards it and informs the service center 30 thereof. Then the service center 30 stores the time stamp and the status (e.g., "period of time for validity of the programming order expired").

Updating the status of transmission of the programming order may be limited to a partial quantity of essential status. Thus, for example, it is possible to refrain from the transmission of the status "intermediate patient device has not been able to successfully transfer the order to the implant for the seventh time."

Figure 3:
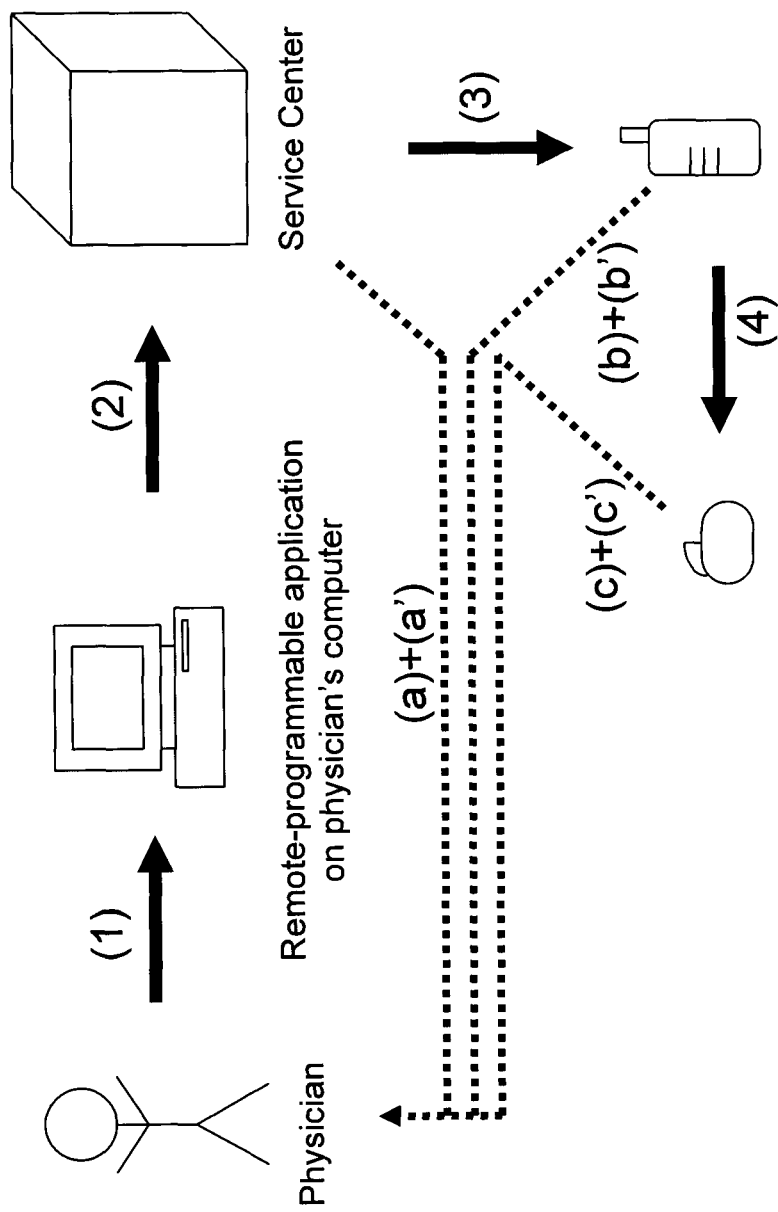
FIG. 3: shows a schematic diagram of remote programming of an implant in the event of success.

FIG. 3 schematically illustrates the case of success:
Step (1): The physician, via the remote programming application at the physician's computer, selects an implant and compiles a program for it.
Step (2): The program is transmitted from the remote programming application at the physician's computer to the service center.
Step (a): The service center confirms correct receipt of the program to the remote programming application.
Step (3): The service center relays the programming to the intermediate patient device.

Step (a'): The service center confirms to the physician that the forwarding to the intermediate patient device has been performed correctly.

Step (4): The intermediate patient device forwards the programming to the implant.

Step (c): The implant confirms to the physician that it has correctly received the reprogramming and later Step (c'): also that reprogramming has been performed correctly.

All the confirmations and status acknowledgement information occur in the same chain in which the information itself has run, but in reverse.

Figure 4:
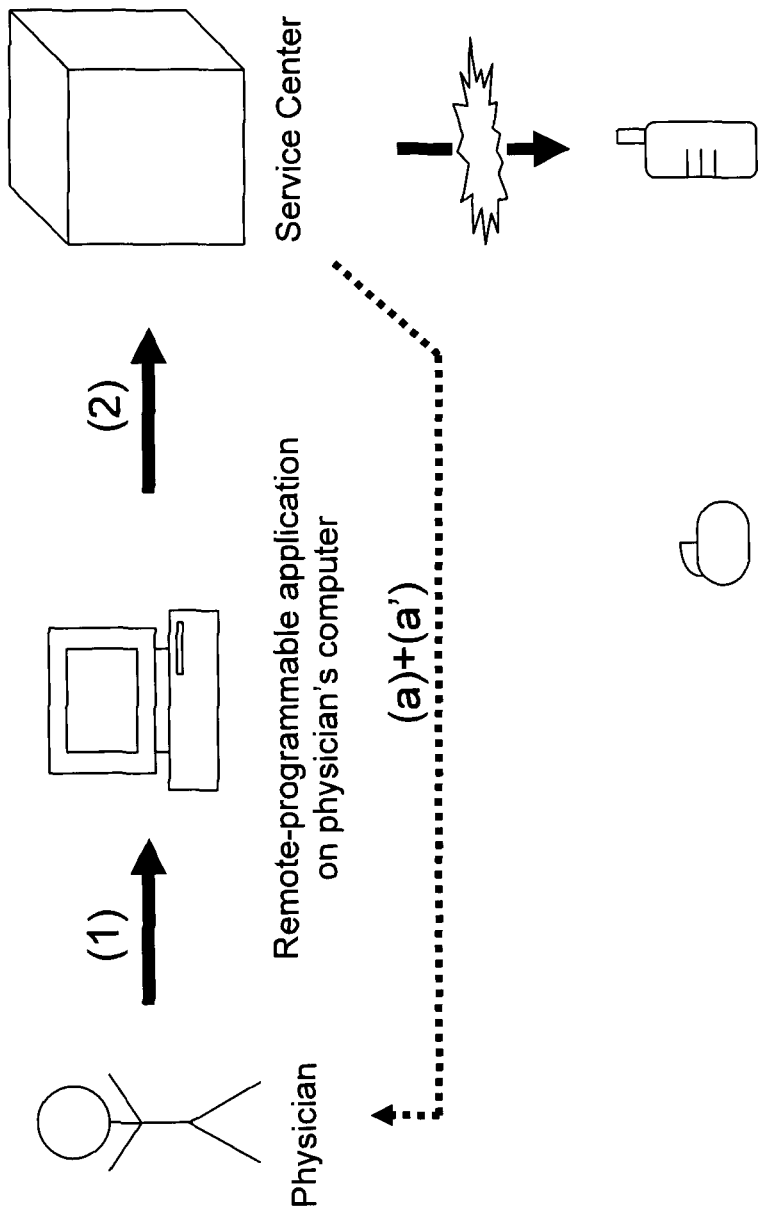
FIG. 4: shows a schematic diagram of remote programming of an implant in the event of an error.

FIG. 4 shows the sequence in the case of a failed transmission:

Step (1): The physician selects an implant and compiles a program for it.

Step (2): The program is transmitted from the physician's computer to the service center.

Step (a): The service center confirms to the remote programming application the correct receipt.

Step (3): The service center forwards the programming to the intermediate patient device. This fails, e.g., because the intermediate patient device cannot be reached or because it did not confirm receipt before arrival of an intended ending point in time for programming.

Step (a'): The service center notifies the physician that the message could not be forwarded and that reprogramming has failed.

The remote programming application is preferably designed so that a physician can mange multiple implants. Accordingly, it has an input unit wherein a respective implant that is to be programmed can be selected, and wherein a programming order for this implant can be compiled.

What is claimed is:

1. A system for remote programming of a programmable personal medical device including:
   a. a programmable personal device (10, 20) and
   b. a service center (30), wherein
   (1) the programmable personal device has:
      (a) a data communications interface providing at least indirect connection of the programmable personal device to the service center (30), and
      (b) a programmable controller controlling functions of the programmable personal device;
   (2) the service center (30) has:
      (a) a data communications interface providing at least indirect connection of the service center (30) to the programmable personal device, and
      (b) a user interface which
         (i) compiles programming orders for the programmable Personal device, and
         (ii) sends compiled programming orders,
   and further wherein:
   I. the service center (30) has a programming monitoring unit (40) which:
      a. determines an ending point in time for programming which depends on the point in time of sending the programming order, and
      b. cancels the programming order or deletes it if the service center (30)has not received a confirmation of programming confirming successful execution of the programming order by the programmable personal device by the ending point in time for programming, and
   II. the programmable personal device sends a confirmation of programming to The service center (30):
      a. after receiving a programming order, or
      b. after successfully forwarding a programming order.

2. The system of claim 1 wherein:
   a. the programmable personal device is an intermediate patient device (20), and
   b. the intermediate patient device (20) includes a short-range wireless interface for data communication with an implant (10).

3. The system of claim 2 wherein the intermediate patient device (20):
   a. forwards a received programming order to an implant (10) assigned to the programmable personal device (20), and
   b. with each forwarding, sends a forwarding confirmation to the service center (30), the forwarding confirmation defining a confirmation of programming.

4. The system of claim 3 wherein the programmable personal device adds a time stamp to the confirmation of programming, the time stamp being at least partially determined by:
   a. the point in time of forwarding of the programming order, or
   b. the point in time of receipt of the programming order.

5. The system of claim 2 wherein the programmable personal device sends a confirmation of receipt to the service center (30) after receipt of a programming order, the confirmation of receipt defining a confirmation of programming.

6. The system of claim 1 wherein the programmable personal device is an implant (10) which, upon receiving a programming order, then sends a confirmation of receipt defining a confirmation of programming.

7. The system of claim 6:
   a. further including an intermediate patient device (20),
   b. wherein:
      (1) the implant (10) has a data communications interface providing bidirectional data communication with the intermediate patient device (20), through which the implant (10) receives a programming order from the intermediate patient device (20), and then sends a confirmation of receipt to the intermediate patient device, and
      (2) the intermediate patient device (20) then forwards a confirmation of receipt of the implant (10) to the central service center (30), the confirmation of receipt defining a confirmation of programming.

8. The system of claim 7 wherein either the implant or the intermediate patient device adds a time stamp to the confirmation of programming.

9. The system of claim 6 wherein the implant (10):
   a. attempts execution of a received programming order, and
   b. in the case of successful execution, sends a message of success to an intermediate patient device,
   wherein the intermediate device thereafter forwards a message of success of the implant to the central service center (30), the message of success defining a confirmation of programming.

10. The system of claim 9 wherein:
    a. the implant (10) also sends a message of failure to the intermediate patient device in the case of unsuccessful execution, and
    b. the intermediate patent device thereafter forwards a message of failure of the implant to the service center (30), the message of failure defining a confirmation of programming.

11. The system of claim 1 wherein the programming monitoring unit (40):
    a. stores the status of the transmission and execution of a programming order, and b. updates the status on the basis of incoming confirmations of programming.

12. The system of claim 11 wherein the programming monitoring unit (40) stores both:
 a. the last status of the transmission and execution of the programming order, and
 b. prior statuses of the transmission and execution of prior programming orders, together with time stamps associated with the statuses.

13. The system of claim 1 wherein the programming monitoring unit (40):
 a. is connected to a database (34), and
 b. determines multiple ending points in time for programming for:
  (1) one or more programmable personal devices, and/or
  (2) one or more transmission steps or execution steps of a programming order, and
 c. assigns corresponding confirmations of programming with time stamps to The multiple ending points.

14. The system of claim 13 wherein the user interface:
 a. is defined by a remote programming application (58) running on a device (50) remote from the service center (30), and
 b. allows programming of multiple different programmable personal devices, and
 c. has an input interface for selection of a programmable personal device, and for compilation of a programming order for a selected programmable personal device.

15. The system of claim 14 wherein the remote programming application (58) has an input unit for entering one or more ending points in time for programming for a respective programming order.

16. A system for remote programming of a programmable personal medical device including:
 a. an implant (10) at least partially situated within the body of a patient; the implant having:
  (1) a programmable controller controlling at least some functions of the implant (10) in accordance with programming orders;
  (2) an implant data communications interface:
   (a) receiving the programming orders to be executed by the programmable controller, and
   (b) sending a confirmation of programming after one or more of:
    i. receipt of the programming orders, and
    ii. successful execution of the programming orders by the programmable controller;
 b. a service center (30) remote from the implant (10), the service center having:
  (1) a service center data communications interface sending the programming orders to the implant data communications interface;
  (2) a programming monitoring unit (40) which:
   a. sets an ending point in time for programming, the ending point being dependent on the point in time at which the service center data communications interface sends the programming orders to the implant data communications interface, and
   b. cancels or deletes the programming orders if the service center (30) has not received the confirmation of programming by the ending point in time for programming.

17. The system of claim 16 further including one or more intermediate devices (20) spaced between the implant (10) and the service center (30), wherein each intermediate device relays programming orders from the service center (30) toward the implant (10).

18. The system of claim 17 wherein each intermediate patient device (20), upon at least one of:
 a. receipt of programming orders from the service center (30), and
 b. forwarding of programming orders toward the implant (10),
 sends a confirmation of programming to the service center (30), wherein the confirmation of programming is indicative of the receipt or forwarding of the programming orders.

19. The system of claim 18 wherein each intermediate patient device (20) adds a time stamp to any confirmation of programming sent by the intermediate patient device (20).

20. The system of claim 17 wherein:
 a. the implant data communications interface provides bidirectional data communication with the intermediate patient device (20), through which the implant (10) receives a programming order from the intermediate patient device (20), and then sends a confirmation of receipt to the intermediate patient device, and
 b. the intermediate patient device (20) then forwards a confirmation of receipt of the implant (10) to the service center (30), the confirmation of receipt defining a confirmation of programming.

\* \* \* \* \*